(12) United States Patent
Hong et al.

(10) Patent No.: US 12,084,402 B2
(45) Date of Patent: Sep. 10, 2024

(54) PREPARATION PROCESS OF DIAZOMETHANE

(71) Applicant: ASYMCHEM LABORATORIES (TIANJIN) CO., LTD., Tianjin (CN)

(72) Inventors: Hao Hong, Morrisville, NC (US); Jiangping Lu, Tianjin (CN); Enxuan Zhang, Tianjin (CN); Wei Shen, Tianjin (CN); Honglei Yan, Tianjin (CN); Zhen Zhang, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 331 days.

(21) Appl. No.: 17/611,712

(22) PCT Filed: May 21, 2019

(86) PCT No.: PCT/CN2019/087761
§ 371 (c)(1),
(2) Date: Nov. 16, 2021

(87) PCT Pub. No.: WO2020/232625
PCT Pub. Date: Nov. 26, 2020

(65) Prior Publication Data
US 2022/0242818 A1    Aug. 4, 2022

(51) Int. Cl.
*C07C 245/16*    (2006.01)
(52) U.S. Cl.
CPC ............................ *C07C 245/16* (2013.01)

(58) Field of Classification Search
None
See application file for complete search history.

(56) References Cited

U.S. PATENT DOCUMENTS 5,459,243 A   10/1995   Acevedo
5,854,405 A   12/1998   Archibald

FOREIGN PATENT DOCUMENTS

CN    105418452 A    3/2016

OTHER PUBLICATIONS

International Search Report for corresponding application PCT/CN2019/087761 filed May 21, 2019; Mail date Feb. 21, 2020.

*Primary Examiner* — Joseph R Kosack
(74) *Attorney, Agent, or Firm* — CANTOR COLBURN LLP

(57) ABSTRACT

Provided is a preparation process of diazomethane. The preparation process includes: step S1, taking N-methylurea as a raw material to continuously prepare, in a continuous reactor, a first product system containing N-methyl-N-nitrosourea: step S2, performing continuous extraction and continuous back-extraction on the first product system to obtain an N-methyl-N-nitrosourea solution; step S3, enabling the N-methyl-N-nitrosourea solution to continuously react with an alkaline solution in a continuous reactor to obtain a second product system containing the diazomethane; and step S4, performing continuously liquid separation, water freezing and removal on the second product system, to obtain the diazomethane.

17 Claims, No Drawings

PREPARATION PROCESS OF DIAZOMETHANE

TECHNICAL FIELD

The disclosure relates to the field of diazomethane preparation, and in particular, to a preparation process of diazomethane.

BACKGROUND

Diazomethane is a yellow gas with a strong pungent odor, is soluble in ethanol and ether, and may cause an explosion while being subjected to heat, fire, friction, and impact. It is very active in nature, capable of performing various types of reactions. It is an important reagent in organic synthesis, and mainly used for methylation reactions of carboxyl, phenolic hydroxyl, enol and the like, homologation reactions for ketone and carboxylic acid in preparation of diazoketone, 1,3 dipolar cycloaddition reaction and the like. In addition, because of its low molecular weight, the reaction in which the diazomethane participates has a good atomic efficiency and nitrogen is the only by-product after the reaction.

However, due to its strong carcinogenicity and toxicity, and extremely easy to explode, the preparation and control of the diazomethane are very difficult in industrial production. The scale of most diazomethane applications is in a laboratory level.

There are three main synthetic routes for the diazomethane:

route₁

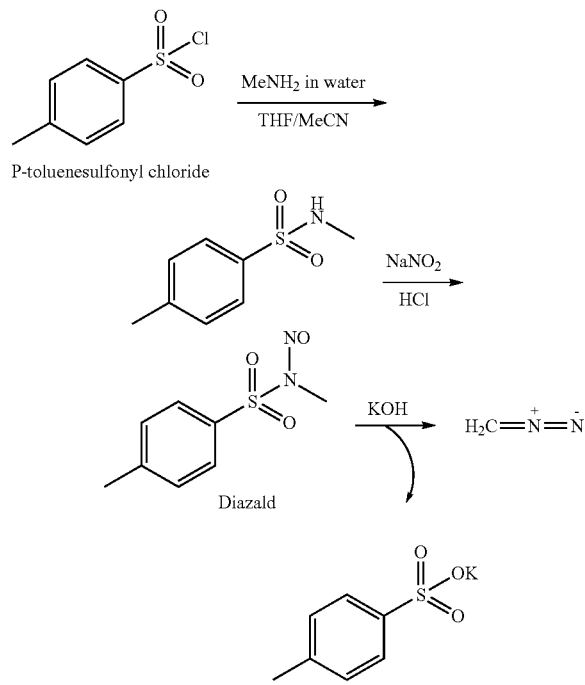

route₂

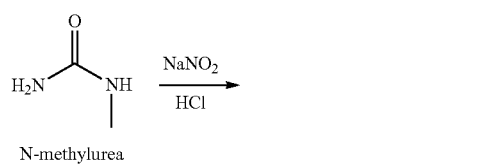

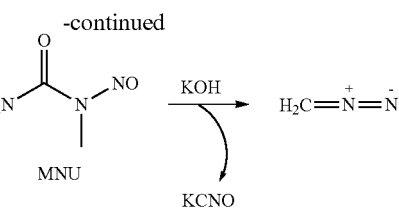

route₃

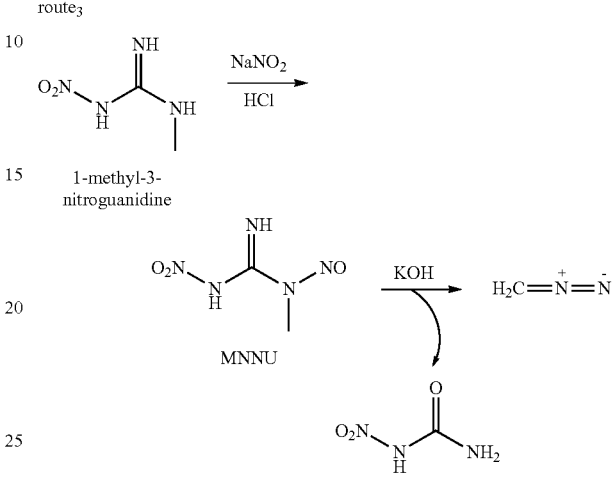

These three routes all generate the diazomethane by a reaction of N-methyl-N-nitroso precursor compound and strong base. The availability and shelf life of such a compound are considered, the three compounds Diazald, MNU and MNNU are generally used as precursors for the preparation of the diazomethane. However, because the toxicity, irritation, carcinogenicity and mutagenicity of MNNU are the strongest among the three precursor compounds, Diazald and MNU are usually used for the preparation of diazomethane at present. The diazomethane prepared in batches needs to be diluted with nitrogen or diluted in ether to form solution before use in order to prevent explosion due to the excessive concentration.

Aerojet-General Corporation (now AMPAC Fine Chemicals) is the first company to carry out large-scale production and application of the diazomethane. It has patents for continuous preparation of diazomethane (U.S. Pat. No. 5,854,405B2) and batch preparation of diazomethane (EP0916649). Its continuous route uses non-toxic N-methylurea as a starting material and continuously reacts with sodium nitrite/hydrochloric acid system to prepare ether solution of the diazomethane precursor MNU, and then reacts with alkali aqueous solution to generate the diazomethane and it is dissolved in an organic solvent. Although the preparation of MNU is a continuous reaction, the preparation of the diazomethane thereof is actually prepared by using three reactors (3000 L), it is essentially a batch reaction. The diazomethane prepared in this way may introduce a small amount of water during a liquid separation process, so this makes it unusable for subsequent reactions that are sensitive to water.

In order to obtain a dry diazomethane gas, Phoenix Chemicals Ltd. develops a pilot-scale preparation process of a diazomethane gas using Diazald as a precursor (Org. Process Res. Dev. 2002, 6, 884). The device may produce 60 tons of the diazomethane per year.

Our company also develops a process for continuous preparation of a diazomethane gas using Diazald as a precursor compound and applies it in kilogram production (CN101844063B).

The above three examples are the existing industrial application examples of the diazomethane. Due to the danger of the large-scale batch synthesis production of the diazomethane, the research and development of its continuous synthesis technology also attract extensive attention.

Rossi E. et al. report that a special heart-shaped coil is used to prepare diazomethane solution with NMU as a raw material, and it is directly fed into a reaction system for methylation of carboxylic acid without separating an alkaline aqueous phase. However, this method is only suitable for a reaction system that is not sensitive to water (Organic Process Research & Development, 2017, 16(5):1146-1149). Carlson E. et al. report that a reaction kettle is used to prepare a diazomethane gas with Diazald as a raw material, and it is directly fed into olefin substrate solution to perform a cycloaddition reaction. Maurya R A et al. report that a dual-channel coil reactor with a polydimethylsiloxane (PMDS) semipermeable membrane is used to prepare and separate a diazomethane gas for a reaction (Synthetic Communications, 2016, 46(1):55-62).

Mastronardi F et al. report a process of using an AF-2400 material as a semipermeable membrane tube in tube with Diazald as a raw material for continuous production and reaction of diazomethane (Organic Letters, 2013, 15(21): 5590-5593). Dallinger D. et al. also report a process of using an AF-2400 material as a semipermeable tube in flask with Diazald as a raw material for continuous preparation and reaction of diazomethane (Journal of Organic Chemistry, 2016, 81(14): 5814-5823). Lehmann H. et al. use a PFA coil and a liquid-liquid separator with a semipermeable membrane structure and use N-methylurea as a raw material, to achieve a two-step full continuous reaction of diazomethane precursor MNU and diazomethane (Green Chemistry, 2016, 19(6), 1449).

It may be seen that the process for preparing the diazomethane in the prior art mainly has the following problems:

(1) Due to the toxicity and explosiveness of the diazomethane itself in batch preparation and amplified production, a safety risk is very high. At present, almost no batch preparation of the diazomethane is used in the industrial production.

(2) The continuous preparation requires the use of the expensive semipermeable membrane or the liquid-liquid separator to separate the diazomethane from the water phase in order to carry out the subsequent reactions sensitive to moisture, so that the device investment is large and the production cost is higher.

SUMMARY

A main purpose of the disclosure is to provide a preparation process for diazomethane, as to solve a problem in the prior art that the cost of a continuous process diazomethane preparation device is high.

In order to achieve the above purpose, according to one aspect of the disclosure, a preparation process of diazomethane is provided, the preparation process includes: step S1, taking N-methylurea as a raw material to continuously prepare, in a continuous reactor, a first product system containing N-methyl-N-nitrosourea; step S2, performing continuous extraction and continuous back-extraction on the first product system to obtain an N-methyl-N-nitrosourea solution; step S3, enabling the N-methyl-N-nitrosourea solution to continuously react with an alkaline solution in a continuous reactor to obtain a second product system containing the diazomethane; and step S4, performing continuously liquid separation, water freezing and removal on the second product system, to obtain the diazomethane.

Further, the above step S1 includes: continuously feeding an acid, a solvent, a sodium nitrite and the N-methylurea to the continuous reactor for reaction to prepare the first product system.

Further, the acid is selected from any one of hydrochloric acid, sulphuric acid, nitric acid, phosphoric acid, formic acid, acetic acid, p-toluenesulfonic acid and methylsulfonic acid, the solvent includes water and an organic solvent, and the organic solvent is selected from any one or more of a group consist of chloroform, dichloromethane, ethyl acetate, tetrahydrofuran, 2-methyltetrahydrofuran, benzene, methylbenzene and dimethylbenzene.

Further, the reaction temperature in the step S1 is 0-120° C. and preferably is 10-30° C., a molar ratio of the N-methylurea, the sodium nitrite and the acid preferably is 1:1.5-2.5:1-2, and a ratio by volume of the water to the organic solvent in the solvent preferably is 1:3-5; and preferably, the retention time in the step S1 is 5-30 minutes.

Further, the above continuous reactor is a continuous coil reactor.

Further, the above step S2 includes: continuously feeding the first product system to a first extraction column and extracting with an extractant to obtain an extraction solution; and continuously feeding the extraction solution to a second extraction column and back-extracting with an alkaline back-extracting solution to obtain the N-methyl-N-nitrosourea solution; and the extractant is selected from any one or more of a group consist of chloroform, dichloromethane, ethyl acetate, tetrahydrofuran, 2-methyltetrahydrofuran, benzene, methylbenzene and dimethylbenzene, the alkaline back-extracting solution is selected from an aqueous solution of any one of a group consist of triethylamine, diisopropyl ethylamine, tert-butylamine, 1,4-diazabicyclo, 1,8-diazabicyclo[5.4.0]undec-7-ene, KOH, NaOH, $K_2CO_3$, $Na_2CO_3$, $NaHCO_3$, $Cs_2CO_3$, $KHCO_3$, sodium acetate and potassium acetate, and preferably the pH value of the extraction system in the back-extraction process is 5-7.

Further, the alkaline solution in the step S3 is a potassium hydroxide solution, a sodium hydroxide solution, a lithium hydroxide solution, a potassium carbonate solution, a sodium carbonate solution, a potassium bicarbonate solution or a sodium bicarbonate solution.

Further, the reaction temperature in the above step S3 is −20-100° C. and preferably is 0-30° C., and the retention time in the step S3 preferably is 30-150 seconds.

Further, the above step S4 includes: continuously feeding the second product system to a third extraction column for liquid separation to obtain an upper layer of overflowed organic solution; and performing freezing treatment on the upper layer of overflowed organic solution to coagulate the water therein to obtain an organic solution of the diazomethane.

Further, the above freezing treatment includes: continuously feeding the upper layer of overflowed organic solution to a continuous reaction kettle, cooling to −30-50° C. with a stirring condition and keeping for 40-80 minutes, wherein the organic solution of the diazomethane is overflowed from an upper layer of the continuous reaction kettle, and preferably a filter screen is disposed at an overflow port of the continuous reaction kettle.

A technical scheme of the disclosure is applied, the safe and non-toxic N-methylurea is used as a raw material, the full continuous reaction and post-treatment are used to obtain the 2-methyltetrahydrofuran solution of the diazomethane precursor MNU, and then the full continuous reaction and post-treatment are directly used again to obtain anhydrous diazomethane solution, herein the freezing process is used to remove the water, the expensive semipermeable membrane or the liquid-liquid separator is avoided from being used. Therefore, the preparation process is safer and more controllable compared with an existing batch diazomethane preparation process; and compared with an existing continuous diazomethane preparation process, the cost is lower.

DETAILED DESCRIPTION OF THE EMBODIMENTS

It is to be noted that embodiments in the present application and features in the embodiments may be combined with each other in the case without conflicting. The disclosure is described in detail below in combination with the embodiments.

As analyzed in the background of the present application, the continuous production of diazomethane in the prior art requires the use of an expensive semipermeable membrane or a liquid-liquid separator to separate the diazomethane from a water phase in order to carry out subsequent reactions that are sensitive to moisture, so that the device investment is large and the production cost is high. In order to solve this problem, the present application provides a preparation process of diazomethane. In a typical embodiment of the present application, the preparation process of the diazomethane includes: step S1, taking N-methylurea as a raw material to continuously prepare, in a continuous reactor, a first product system containing N-methyl-N-nitrosourea; step S2, performing continuous extraction and continuous back-extraction on the first product system to obtain an N-methyl-N-nitrosourea solution; step S3, enabling the N-methyl-N-nitrosourea solution to continuously react with an alkaline solution in a continuous reactor to obtain a second product system containing the diazomethane; and step S4, performing continuously liquid separation, water freezing and removal on the second product system, to obtain the diazomethane.

The above preparation process of the present application uses safe and non-toxic N-methylurea as a raw material, the full continuous reaction and post-treatment are used to obtain the 2-methyltetrahydrofuran solution of the diazomethane precursor MNU, and then the full continuous reaction and post-treatment are directly used again to obtain anhydrous diazomethane solution, herein the freezing process is used to remove the water, the expensive semipermeable membrane or the liquid-liquid separator is avoided from being used. Therefore, the preparation process is safer and more controllable compared with an existing batch diazomethane preparation process; and compared with an existing continuous diazomethane preparation process, the cost is lower. Specifically:

The preparation process of the present application does not use an expensive water-removing membrane or device, and may obtain diazomethane solution with extremely low water content in a lower cost, and may directly react with a water-sensitive material or system;

the low-cost, non-toxic N-methylurea is used as a starting material, the MNU obtained by the continuous preparation may be directly used for the continuous preparation of the diazomethane in the second step without separation and purification, a risk of contacting with the easy-carcinogenic and easy-allergic material MNU is reduced, and compared with most reactions that use Diazald as a precursor of the diazomethane, the cost is lower and the three wastes are less;

unique properties of a continuous device (a reaction system is small, and a heat exchange speed is much higher than that of a batch device) make the safety higher than that of a batch reaction even if a reaction condition is more severe; and the unique properties of the continuous process, almost no amplification effect in production, are suitable for industrialization to reproduce a small trial yield.

A reaction mechanism for preparing the MNU by using the N-methylurea as the raw material in the present application is the same as the prior art. Preferably, the above step S1 includes: continuously feeding an acid, a solvent, a sodium nitrite and the N-methylurea to the continuous reactor for reaction to prepare the first product system. The above N-methylurea is firstly dissolved in water and acid (added in a mode of aqueous solution), and then mixed solution of the acid, the water and the N-methylurea is continuously fed, and the sodium nitrite is also continuously fed in a state of aqueous solution. The solvent includes a solvent for dissolving the sodium nitrite and the N-methylurea.

The acid and the solvent used in the present application may be selected from common acids and solvents in the prior art that use the N-methylurea as the raw material. In order to better adapt to the continuous reaction, preferably the acid is selected from any one of hydrochloric acid, sulphuric acid, nitric acid, phosphoric acid, formic acid, acetic acid, p-toluenesulfonic acid and methylsulfonic acid, the solvent includes water and an organic solvent, and the organic solvent is selected from any one or more of a group consist of chloroform, dichloromethane, ethyl acetate, tetrahydrofuran, 2-methyltetrahydrofuran, benzene, methylbenzene and dimethylbenzene. The solvent contains the water and the organic solvent at the same time, and the both form a stratification effect, it is beneficial to the separation of a product from the reaction system.

The above reaction temperature for preparing the MNU may refer to the prior art. Preferably, the reaction temperature in the step S1 is 0-120° C., more preferably 10-30° C., as to guarantee the stability of the reaction. In addition, in order to improve a conversion rate and further guarantee the safety, preferably a molar ratio of the N-methylurea, the sodium nitrite and the acid is 1:1.5-2.5:1-2, the molar ratio may be achieved by adjusting a raw material ratio or a pump speed of each material; and preferably a volume ratio of the water and the organic solvent in the solvent is 1:3-5, as to improve a separation efficiency of the product. In addition, in order to increase the conversion rate of the material while improving the reaction efficiency, preferably retention time of the above step S1 is 5-30 min.

The continuous reactor used in the preparation process may be a tubular continuous reactor or a kettle-type continuous reactor commonly used in the prior art, and there is no need to configure a semipermeable membrane. Preferably, the continuous reactor is a continuous coil reactor.

In an embodiment of the present application, the step S2 includes: continuously feeding the first product system to a first extraction column and extracting with an extractant to obtain an extraction solution; and continuously feeding the extraction solution to a second extraction column and back-extracting with an alkaline back-extracting solution to obtain the N-methyl-N-nitrosourea solution, herein the extractant is selected from any one or more of a group consist of chloroform, dichloromethane, ethyl acetate, tetrahydrofuran, 2-methyltetrahydrofuran, benzene, methylbenzene and dimethylbenzene, the alkaline back-extracting solution is selected from an aqueous solution of any one of triethylamine, diisopropyl ethylamine, tert-butylamine, 1,4-diazabicyclo (DABCO), 1,8-diazabicyclo[5.4.0]undec-7-ene (DBU), KOH, NaOH, $K_2CO_3$, $Na_2CO_3$, $NaHCO_3$, $Cs_2CO_3$, $KHCO_3$, sodium acetate and potassium acetate, and preferably the pH value of the extraction system in the back-extraction process is 5-7. The first extraction column achieves continuous extraction and separation of the first product system, and uses its continuity to achieve the industrialized production without using the expensive liquid-liquid separator. After the extraction and separation, the alkaline solution is used for the back-extraction, and the efficient recovery of the MNU is achieved.

A principle of preparing the diazomethane by the MNU in the present application is also the same as the prior art. Preferably, the alkaline solution in the step S3 is a potassium hydroxide solution, a sodium hydroxide solution, a lithium hydroxide solution, a potassium carbonate solution, a sodium carbonate solution, a potassium bicarbonate solution or a sodium bicarbonate solution.

The reaction temperature of the above step S3 may also refer to the prior art. For example, the reaction temperature of the above step S3 is −20-100° C., and preferably 0-30° C. In order to improve the reaction efficiency, preferably a retention time of the step S3 is 30-150 seconds.

After the above reaction is completed, the water therein needs to be separated to be suitable for a water-sensitive reaction. Preferably, the step S4 includes: continuously feeding the second product system to a third extraction column for liquid separation to obtain an upper layer of overflowed organic solution; and performing freezing treatment on the upper layer of overflowed organic solution to coagulate the water therein to obtain an organic solution of the diazomethane. After the extraction column is used for the liquid separation treatment, most of the water in the second product system is separated, and then the different freezing points of the water and the diazomethane are used to perform the freezing treatment so that the water therein is frozen, thereby the organic solution of the diazomethane is obtained.

In an embodiment of the present application, the freezing treatment includes: continuously feeding the upper layer of overflowed organic solution to a continuous reaction kettle, cooling to −30-50° C. with a stirring condition and keeping for 40-80 minutes, herein the organic solution of the diazomethane is overflowed from an upper layer of the continuous reaction kettle, and preferably a filter screen is disposed at an overflow port of the continuous reaction kettle. The freezing is performed with the stirring condition, it is beneficial to the full separation of the moisture and organic matter; in addition, because the upper layer of the overflowed organic solution is continuously fed, the organic solution of the diazomethane can overflow from the continuous reaction kettle after the freezing treatment. In order to avoid entrainment of flake ice in the overflow, the filter screen is installed at the overflow port to intercept the flake ice, thereby the efficiency of water removal is improved.

The beneficial effects of the present application are further described below in combination with embodiments and contrast examples.

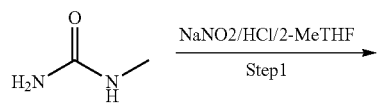

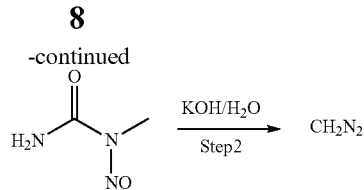

Embodiment 1

Configuration of a material beating system A: 100 g of N-methylurea was added to a material beater bottle A, 100 ml of water was added, 266 g of 37% hydrochloric acid was slowly added, and stirred until it was dissolved.

Configuration of a material beating system B: 1750 mL of 2-Me-THF was added to a material beating bottle B.

Configuration of a material beating system C: 140 g of sodium nitrite was added to a material beating bottle C, 400 mL of water was added, and stirred until it was dissolved.

Configuration of a material beating system D: 600 mL of 2-Me-THF was added to a material beating bottle D.

Configuration of a material beating system E: potassium bicarbonate was added to a material beating bottle E, 654 ml of water was added, and stirred until it was dissolved.

Device preparation: about 500 mL of tap water was added to a first extraction column to a half height of the column; and about 200 mL of potassium bicarbonate aqueous solution was added to a second extraction column to ¼ of the column height.

200 mL of a first tetrafluoro-coil reactor was filled with the tap water to 23-27° C. (target temperature 25° C.). After the temperature is stabilized for 10 minutes, material beating may be carried out.

Material beating: the material beating bottle A, the material beating bottle B and the material beating bottle C were connected to a four-way of the 200 mL first tetrafluoro-coil reactor, and a material beating pump A, a material beating pump B and a material beating pump C were installed on respective connecting pipelines. The material beating pump A, the material beating pump B and the material beating pump C were opened, and respective flow rates were controlled to be 3.57 g/min, 11.42 g/min, and 4.11 g/min, three materials were merged at the four-way and enter the first tetrafluoro-coil reactor for reaction, and retention time was 10 minutes.

Extraction: the first tetrafluoro-coil reactor was connected with an upper end of the first extraction column, the material beating bottle D was connected with a lower end of the first extraction column, and a material beating pump D was installed on a connecting pipeline, and the material beating pump D was started to pump 600 mL of 2-Me-THF from the lower end of the first extraction column for continuous back-extraction. A flow rate of the material beating pump D is: 3.95 g/min. The lower end of the first extraction column released an aqueous phase, and an organic phase of the upper end entered the second extraction column. During an extraction process, an effective liquid holding capacity of the first extraction column was controlled to ~400 mL, and theoretical RT=30 minutes.

Back-extraction: the organic phase from the upper end of the first extraction column was pumped in from the lower end of the second extraction column, a material beating bottle E was connected with the upper end of the second extraction column and a material beating pump E was installed on a connecting pipe, the material beating pump E was started to continuously pump potassium bicarbonate solution (163 g potassium bicarbonate+654 mL water) into the second extraction column for continuously adjusting the pH between 5 and 7, a flow rate of the material beating pump E was: 4.0 ml/min, and the lower end discharged the aqueous phase. During a back-extraction process, a liquid holding capacity of the second extraction column was controlled to ~400 mL, and theoretical RT=20 minutes.

Material receiving: the organic phase of the second extraction column was received, and a yield of QNMR was measured to be 81% and a pH value was 6.4, herein a measurement method was to use deuterated chloroform to dissolve a sample, mesitylene was added as an internal standard substance, and then proceeded NMR analysis.

Configuration of a material beating system F: the 2-methyltetrahydrofuran solution of the organic phase N-nitroso-N-methylurea obtained above was added into a material beating bottle F.

Configuration of a material beating system G: potassium hydroxide was dissolved in water, and stirred until solids were dissolved, and it was prepared into 15% wt of solution.

Device preparation: tap water was added to a third extraction column to a half height of the column.

A part of potassium hydroxide solution was fed into 20 mL of a second tetrafluoro-coil reactor until a place where the two materials were converged was filled with the potassium hydroxide solution. The second tetrafluoro-coil reactor was placed in an ice water bath, and the temperature is controlled to 0-5° C.

Material beating: the material beating bottle F and the material beating bottle G were connected with a three-way of the 200 mL second tetrafluoro-coil reactor and a material beating pump F and a material beating pump G were installed on respective connecting pipes, the material beating pump F and the material beating pump G were opened, and respective flow rates were controlled to 14.75 g/min and 5.25 g/min, two materials were merged at the three-way, and then enter the 200 mL second tetrafluoro coil reactor for reaction, and retention time was 1 min.

Liquid separation and water removal: the second tetrafluoro coil reactor was connected with an upper end of the third extraction column so that a second product system of the second tetrafluoro coil reactor performed the liquid separation in the second extraction column, and the upper layer of a yellow organic phase overflowed into CSTR at −40° C. and it was stirred for 1 h to freeze and remove the water. The water was frozen into ice at a low temperature so that it was separated from the system. Organic solution of the upper layer of the diazomethane was overflowed through an overflow port with a filter screen, herein a product obtained was verified to be the diazomethane by nuclear magnetism, the water content was detected by Karl Fischer (KF) moisture analyzer, and an HPLC external standard was measured after derivatization with excess benzoic acid. A yield is 57%. The obtained diazomethane solution may directly overflow into mixed anhydride solution to prepare diazoketone.

Embodiment 2

A difference from Embodiment 1 was that the upper layer of the yellow organic phase overflowed into the CSTR at −50° C. during the liquid separation and water removal process and it was stirred for 40 minutes to freeze and remove water. The water was frozen into ice at a low temperature so that it was separated from the system, and the organic solution of the upper layer of diazomethane was overflowed through an overflow port with a filter screen.

Embodiment 3

A difference from Embodiment 1 was that the upper layer of the yellow organic phase overflowed into the CSTR at −30° C. during the liquid separation and water removal process and it was stirred for 80 minutes to freeze and remove water. The water was frozen into ice at a low temperature so that it was separated from the system, and the organic solution of the upper layer of diazomethane was overflowed through an overflow port with a filter screen.

Embodiment 4

A difference from Embodiment 1 was that the acid in the material beating bottle A was 162 g of an acetic acid, and a material beating speed of the material beating pump A was 2.77 g/min.

Embodiment 5

A difference from Embodiment 1 was that the acid in the material beating bottle A was acid solution obtained by using 464 g of p-toluenesulfonic acid dissolved in 693 g of water, and a material beating speed of the material beating pump A was 9.63 g/min.

Embodiment 6

A difference from Embodiment 1 was that 1750 mL of dichloromethane was in the material beating bottle B, and the solvent in the material beating bottle D was 388 mL of dichloromethane.

Embodiment 7

A difference from Embodiment 1 was that toluene was in the material beating bottle B, and the solvent in the material beating bottle D was toluene.

Embodiment 8

A difference from Embodiment 1 was that 1750 mL of ethyl acetate was in the material beating bottle B, and the solvent in the material beating bottle D was 573 ml of ethyl acetate.

Embodiment 9

A difference from Embodiment 1 was that the temperature of the first tetrafluoro coil reactor was about 50° C.

Embodiment 10

A difference from Embodiment 1 was that the temperature of the first tetrafluoro coil reactor was about 120° C.

Embodiment 11

A difference from Embodiment 1 was that the temperature of the first tetrafluoro coil reactor was about 10° C.

Embodiment 12

A difference from Embodiment 1 was that the temperature of the first tetrafluoro coil reactor was about 0° C.

Embodiment 13

A difference from Embodiment 1 was that the retention time in the first tetrafluoro coil reactor was 5 minutes.

Embodiment 14

A difference from Embodiment 1 was that the retention time in the first tetrafluoro coil reactor was 30 minutes.

Embodiment 15

A difference from Embodiment 1 was that the alkaline solution in the material beating pump E was triethylamine.

Embodiment 16

A difference from Embodiment 1 was that the alkaline solution in the material beating pump E was DBU.

Embodiment 17

A difference from Embodiment 1 was that the alkaline solution in the material beating pump E was potassium hydroxide.

Embodiment 18

A difference from Embodiment 1 was that the alkaline solution in the material beating pump E was potassium carbonate.

Embodiment 19

A difference from Embodiment 1 was that the temperature of the second tetrafluoro coil reactor was about −20° C., and the retention time was 150 seconds.

Embodiment 20

A difference from Embodiment 1 was that the temperature of the second tetrafluoro coil reactor was about 30° C.

Embodiment 21

A difference from Embodiment 1 was that the temperature of the second tetrafluoro coil reactor was about 100° C., and the retention time was 30 seconds.

Embodiment 22

A difference from Embodiment 1 was that the temperature of the second tetrafluoro coil reactor was about −10° C., and the retention time was 180 seconds.

Embodiment 23

A difference from Embodiment 1 was that 200 g of 37% hydrochloric acid was added to the material beating bottle A.

Embodiment 24

A difference from Embodiment 1 was that 333 g of 37% hydrochloric acid was added to the material beating bottle A.

Embodiment 25

A difference from Embodiment 1 was that 380 g of 37% hydrochloric acid was added to the material beating bottle A.

Embodiment 26

A difference from Embodiment 1 was that the amount of sodium nitrite in the material beating bottle C was 93.1 g, the amount of water was still 400 g, and a material beating speed of the material beating bottle C was 3.82 g/min.

Embodiment 27

A difference from Embodiment 1 was that the amount of sodium nitrite in the material beating bottle C was 186.3 g, the amount of water was still 400 g, and a material beating speed of the material beating bottle C was 4.38 g/min.

Embodiment 28

A difference from Embodiment 1 was that the material beating system B was 1500 mL of 2-MeTHF, and respective flow rates of the material beating bottle A, the material beating bottle B and the material beating bottle C were 3.88 g/min, 10.73 g/min, and 4.49 g/min. min.

Embodiment 29

A difference from Embodiment 1 was that the material beating system B was 2500 ml of 2-MeTHF, and respective flow rates of the material beating bottle A, the material beating bottle B and the material beating bottle C were 2.82 g/min, 13.01 g/min, and 3.27 g/min.

The method of Embodiment 1 is used to measure the yield of MNU, the yield of diazomethane, and the water content in the above embodiments. Results of the measurement are shown in Table 1.

TABLE 1

|  | MNU yield (%) | Diazomethane yield (%) | Water content (ppm) |
|---|---|---|---|
| Embodiment 1 | 81 | 57 | 453 |
| Embodiment 2 | 81 | 57 | 501 |
| Embodiment 3 | 81 | 57 | 700 |
| Embodiment 4 | 65 | 54 | 429 |
| Embodiment 5 | 42 | 55 | 490 |
| Embodiment 6 | 75 | 58 | 460 |
| Embodiment 7 | 55 | 30 | 431 |
| Embodiment 8 | 72 | 45 | 476 |
| Embodiment 9 | 60 | 55 | 402 |
| Embodiment 10 | 37 | 49 | 458 |
| Embodiment 11 | 79 | 56 | 442 |
| Embodiment 12 | 77 | 55 | 435 |
| Embodiment 13 | 62 | 58 | 481 |
| Embodiment 14 | 80 | 54 | 488 |
| Embodiment 15 | 80 | 21 | 416 |
| Embodiment 16 | 81 | 44 | 493 |
| Embodiment 17 | 79 | 56 | 443 |
| Embodiment 18 | 81 | 41 | 402 |
| Embodiment 19 | 76 | 36 | 451 |
| Embodiment 20 | 80 | 25 | 480 |
| Embodiment 21 | 81 | 14 | 403 |
| Embodiment 22 | 79 | 39 | 437 |
| Embodiment 23 | 76 | 55 | 454 |
| Embodiment 24 | 80 | 56 | 453 |
| Embodiment 25 | 79 | 50 | 456 |
| Embodiment 26 | 60 | 50 | 452 |
| Embodiment 27 | 80 | 55 | 452 |
| Embodiment 28 | 62 | 57 | 434 |
| Embodiment 29 | 80 | 56 | 410 |

It may be seen from the above descriptions that the above embodiments of the disclosure achieve the following technical effects.

The above preparation process of the present application uses safe and non-toxic N-methylurea as a raw material, the full continuous reaction and post-treatment are used to obtain the 2-methyltetrahydrofuran solution of the diazomethane precursor MNU, and then the full continuous reaction and post-treatment are directly used again to obtain anhydrous diazomethane solution, herein the freezing process is used to remove the water, the expensive semipermeable membrane or the liquid-liquid separator is avoided from being used. Therefore, the preparation process is safer and more controllable compared with an existing batch diazomethane preparation process; and compared with an existing continuous diazomethane preparation process, the cost is lower.

The above are only the preferred embodiments of the disclosure, and are not used to limit the disclosure. Various modifications and changes may be made to the disclosure by those skilled in the art. Any modifications, equivalent replacements, improvements and the like made within the spirit and principle of the disclosure should be included in the scope of protection of the disclosure.

What claimed is:

1. A preparation process of diazomethane, comprising:
    step S1, continuously feeding an acid, a solvent, a sodium nitrite and N-methylurea to the continuous reactor for reaction to prepare a first product system containing N-methyl-N-nitrosourea;
    step S2, performing continuous extraction and continuous back-extraction on the first product system to obtain an N-methyl-N-nitrosourea solution;
    step S3, enabling the N-methyl-N-nitrosourea solution to continuously react with an alkaline solution in a continuous reactor to obtain a second product system containing the diazomethane; and
    step S4, performing continuously liquid separation, water freezing and removal on the second product system, to obtain the diazomethane.

2. The preparation process as claimed in claim 1, wherein the acid is selected from any one of hydrochloric acid, sulphuric acid, nitric acid, phosphoric acid, formic acid, acetic acid, p-toluenesulfonic acid and methylsulfonic acid, the solvent comprises water and an organic solvent, and the organic solvent is selected from any one or more of chloroform, dichloromethane, ethyl acetate, tetrahydrofuran, 2-methyltetrahydrofuran, benzene, methylbenzene and dimethylbenzene.

3. The preparation process as claimed in claim 1, wherein a reaction temperature in the step S1 is 0-120° C.

4. The preparation process as claimed in claim 1, wherein the continuous reactor is a continuous coil reactor.

5. The preparation process as claimed in claim 1, wherein the step S2 comprises:
    continuously feeding the first product system to a first extraction column and extracting with an extractant to obtain an extraction solution; and
    continuously feeding the extraction solution to a second extraction column and back-extracting with an alkaline back-extracting solution to obtain the N-methyl-N-nitrosourea solution; and
    the extractant is selected from any one or more of a group consist of chloroform, dichloromethane, ethyl acetate, tetrahydrofuran, 2-methyltetrahydrofuran, benzene, methylbenzene and dimethylbenzene, the alkaline back-extracting solution is selected from an aqueous solution of any one of triethylamine, diisopropyl ethylamine, tert-butylamine, 1,4-diazabicyclo, 1,8-diazabicyclo[5.4.0]undec-7-ene, KOH, NaOH, $K_2CO_3$, $Na_2CO_3$, $NaHCO_3$, $Cs_2CO_3$, $KHCO_3$, sodium acetate and potassium acetate.

6. The preparation process as claimed in claim 1, wherein the alkaline solution in the step S3 is a potassium hydroxide solution, a sodium hydroxide solution, a lithium hydroxide solution, a potassium carbonate solution, a sodium carbonate solution, a potassium bicarbonate solution or a sodium bicarbonate solution.

7. The preparation process as claimed in claim 1, wherein a reaction temperature in the step S3 is −20-100° C.

8. The preparation process as claimed in claim 1, wherein the step S4 comprises:
    continuously feeding the second product system to a third extraction column for liquid separation to obtain an upper layer of overflowed organic solution; and
    performing freezing treatment on the upper layer of overflowed organic solution to coagulate the water therein to obtain an organic solution of the diazomethane.

9. The preparation process as claimed in claim 8, wherein the freezing treatment comprises:
    continuously feeding the upper layer of overflowed organic solution to a continuous reaction kettle, cooling to −30-50° C. with a stirring condition and keeping for 40-80 minutes, wherein the organic solution of the diazomethane is overflowed from an upper layer of the continuous reaction kettle.

10. The preparation process as claimed in claim 3, wherein the reaction temperature in the step S1 is 10-30° C.

11. The preparation process as claimed in claim 3, wherein a molar ratio of the N-methylurea, the sodium nitrite and the acid is 1:1.5-2.5:1-2.

12. The preparation process as claimed in claim 3, wherein a ratio by volume of the water to the organic solvent in the solvent is 1: 3-5.

13. The preparation process as claimed in claim 3, wherein a retention time in the step S1 is 5-30 minutes.

14. The preparation process as claimed in claim 5, wherein a pH value of the extraction system in the back-extraction process is 5-7.

15. The preparation process as claimed in claim 7, wherein the reaction temperature in the step S3 is 0-30° C.

16. The preparation process as claimed in claim 7, wherein a retention time in the step S3 is 30-150 seconds.

17. The preparation process as claimed in claim 9, wherein a filter screen is disposed at an overflow port of the continuous reaction kettle.

* * * * *